United States Patent

Urbahns et al.

[11] Patent Number: 5,530,014
[45] Date of Patent: Jun. 25, 1996

[54] CYCLOHEXADIENE DERIVATIVES

[75] Inventors: Klaus Urbahns, Wuppertal; Hans-Georg Heine, Krefeld; Bodo Junge, Wuppertal; Rudolf Schohe-Loop, Wuppertal; Hartmund Wollweber, Wuppertal; Henning Sommermeyer, Köln; Thomas Glaser, Overath; Reilinde Wittka, Köln; Jean-Marie-Viktor De Vry, Rösrath, all of Germany

[73] Assignee: Bayer Aktiengesellschaft, Leverkusen, Germany

[21] Appl. No.: 516,679

[22] Filed: Aug. 18, 1995

[30] Foreign Application Priority Data

Aug. 25, 1994 [DE] Germany .................. 44 30 090.5

[51] Int. Cl.⁶ .................. A61K 31/44; A61K 31/275; C07D 213/84; C07C 229/34
[52] U.S. Cl. .................. 514/344; 514/345; 514/349; 514/519; 514/524; 514/523; 546/286; 546/292; 546/293; 546/296; 546/297; 546/307; 546/304; 546/329; 546/345; 546/350; 558/404; 558/408; 558/409; 560/47; 560/18; 560/10; 560/21; 560/48; 562/426; 562/433; 562/435

[58] Field of Search .................. 560/21, 48, 47, 560/18, 10; 546/304, 329, 345, 350, 286, 292, 293, 296, 297, 307; 562/433, 435, 426; 558/404, 408, 409; 514/344, 345, 349, 519, 524, 523

[56] References Cited

PUBLICATIONS

K. Take, et al., Chem. Pharm. Bull., vol. 39, No. 11, pp. 2915–2923, (1991).

T. J. O'Dell, et al., Neuroscience Letters, vol. 94, pp. 93–98, (1988).

Primary Examiner—José G. Dees
Assistant Examiner—Joseph M. Conrad, III
Attorney, Agent, or Firm—Sprung Horn Kramer & Woods

[57] ABSTRACT

The cyclohexadiene derivatives are prepared by reaction of cyclohexanones with amines and subsequent dehydration. The compounds are suitable as active compounds in medicaments on account of their property of being selective modulators of calcium channel-dependent potassium channels.

6 Claims, No Drawings

CYCLOHEXADIENE DERIVATIVES

The present invention relates to cyclohexadiene derivatives, a process for their preparation and their use as medicaments, in particular as cerebrally active agents.

It is already known that 3,6-cyclohexadiene-2-phenyl-1,3-dicarboxylic acid esters have a muscle contraction-inhibiting action [cf. for this Chem. Pharm. Bull., 39 (11), 2915–23, 1991; GB 87-18906 870810/GB 87-19441 870817].

The invention relates to cyclohexadiene derivatives of the general formulae (Ia and b), $$\underset{R^2R^3N}{\overset{D}{\diagdown}}\overset{A}{\underset{CH_3}{\diagup}}COOR^1 \quad (Ia)$$

$$\underset{R^2R^3N}{\overset{D}{\diagdown}}\overset{A}{\underset{CH_3}{\diagup}}COOR^1 \quad (Ib)$$

in which

A represents aryl having 6 to 10 carbon atoms or pyridyl, each of which is optionally substituted up to 3 times by identical or different substituents from the group consisting of nitro, cyano, cycloalkyl having 3 to 7 carbon atoms, halogen and trifluoromethyl or straight-chain or branched alkylthio, alkyl or alkoxy in each case having up to 6 carbon atoms, $R^1$ represents hydrogen or straight-chain or branched alkyl having up to 8 carbon atoms, $R^2$ and $R^3$ are identical or different and represent hydrogen or straight-chain or branched alkyl or acyl in each case having up to 6 carbon atoms, D represents nitro or straight-chain or branched alkoxycarbonyl having up to 8 carbon atoms, and their salts.

Preferred salts are physiologically acceptable salts. In general, these are salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example acetic acid, malic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds according to the invention can exist in stereoisomeric forms which behave either as image and mirror image (enantiomers) or which do not behave as image and mirror image (diastereomers). The invention relates both to the antipodes and to the racemic forms as well as the diastereomer mixtures. Like the diastereomers, the racemic forms can also be separated into the stereoisomerically uniform constituents in a known manner.

Preferred compounds of the general formula (Ia or b) are those in which

A represents phenyl, naphthyl or pyridyl, each of which is optionally substituted up to 3 times by identical or different substituents from the group consisting of nitro, cyano, fluorine, chlorine, bromine, iodine, cyclopentyl, cyclohexyl and trifluoromethyl or straight-chain or branched alkylthio, alkyl or alkoxy in each case having up to 4 carbon atoms, $R^1$ represents hydrogen or straight-chain or branched alkyl having up to 6 carbon atoms, $R^2$ and $R^3$ are identical or different and represent hydrogen or straight-chain or branched alkyl or acyl in each case having up to 4 carbon atoms, D represents straight-chain or branched alkoxycarbonyl having up to 6 carbon atoms, and their salts.

Particularly preferred compounds of the general formula (Ia or b) are those in which A represents phenyl or pyridyl, each of which is optionally substituted up to 3 times by identical or different substituents from the group consisting of nitro, cyano, fluorine, chlorine, bromine, iodine, trifluoromethyl, cyclohexyl, methyl and methoxy or methylthio, $R^1$ represents hydrogen or straight-chain or branched alkyl having up to 4 carbon atoms, $R^2$ and $R^3$ are identical or different and represent hydrogen or straight-chain or branched alkyl or acyl in each case having up to 3 carbon atoms, D represents straight-chain or branched alkoxycarbonyl having up to 4 carbon atoms, and their salts.

A process for the preparation of the compounds of the general formula (Ia or b) according to the invention has been found, characterized in that compounds of the general formula (II)

$$\underset{O}{\overset{D}{\diagdown}}\overset{A}{\underset{OH}{\diagup}}\overset{CO_2R^{1'}}{\underset{CH_3}{}} \quad (II)$$

in which

A and D have the meaning specified, and $R^{1'}$ has the meaning specified for $R^1$, but does not represent hydrogen, are first converted by reaction with amines of the general formula (III)

$$R^2R^3NH \quad (III)$$

in which $R^2$ and $R^3$ have the meaning specified above, in inert solvents and in the presence of an auxiliary into the compounds of the general formula (IV)

$$\underset{R^2R^3N}{\overset{D}{\diagdown}}\overset{A}{\underset{OH\ CH_3}{\diagup}}CO_2R^{1'} \quad (IV)$$

in which

A, D, $R^{1'}$, $R^2$ and $R^3$ have the meaning specified above, and in a second step reacted in an inert solvent, if appropriate in the presence of a base, and in the presence of a dehydrating auxiliary, and the double bond isomers obtained in this process are separated by chromatography and/or crystallization, and if $R^1$=H, the esters are hydrolysed by customary methods, and if $R^2$ and/or $R^3$≠H, an alkylation or acylation is carried out.

The process according to the invention can be illustrated by way of example by the following reaction scheme:

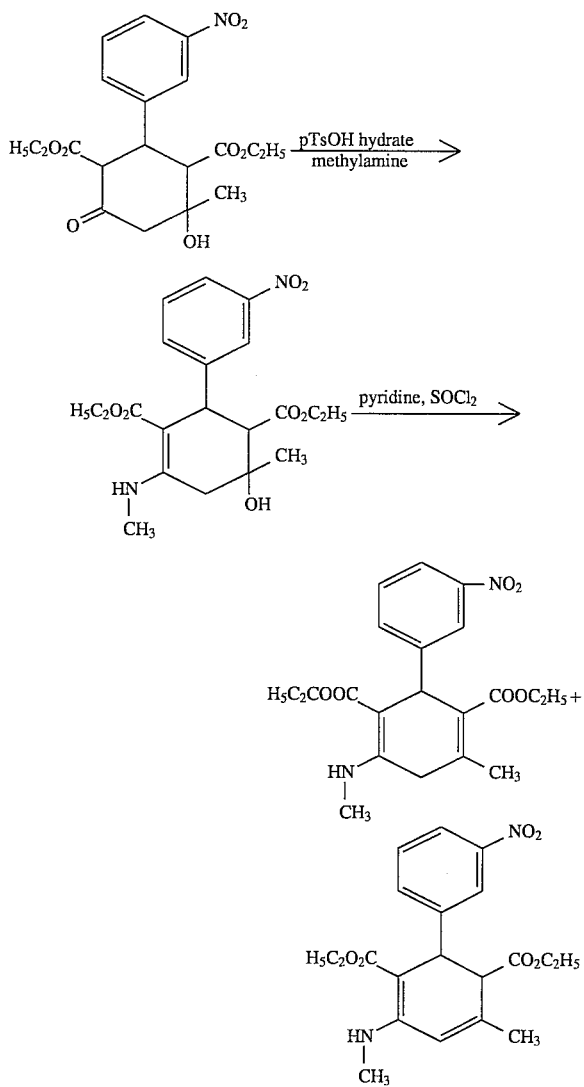

Suitable solvents for the two process steps are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoramide or dimethylformamide, or halogenated hydrocarbon such as methylene chloride or carbon tetrachloride, or hydrocarbons such as benzene or toluene, or pyridine. It is also possible to use mixtures of the solvents mentioned. Toluene is particularly preferred for the first step and pyridine for the second step.

In general, the amine is employed in an amount from 1 mol to 5 mol, preferably from 1 mol to 2 mol, relative to 1 mol of the compounds of the general formula (II).

Suitable auxiliaries for the reaction of the compounds of the general formula (II) are in general organic sulphonic acids, such as p-toluenesulphonic acid, or anhydrous mineral acid such as phosphoric acid or sulphuric acid. p-Toluenesulphonic acid hydrate is preferred.

The auxiliary is employed in an amount from 0.1 mol to 1 mol, preferably from 0.1 mol to 0.2 mol, in each case relative to 1 mol of the compounds of the general formulae (III) and (II).

The reaction with amines of the general formula (III) is in general carried out in a temperature range from 10° C. to 150° C., preferably from 40° C. to 80° C.

The reactions can be carried out at normal pressure, but also at elevated or reduced pressure (e.g. 0.5 to 3 bar). In general, the reaction is carried out at normal pressure.

Suitable auxiliaries for the reaction with the compounds of the formula (IV) are carbodiimides such as, for example, diisopropylcarbodiimide, dicyclohexylcarbodiimide or N-(3-dimethylaminopropyl)-N'-ethylcarbodiimide hydrochloride, or carbonyl compounds such as carbonyldiimidazole or 1,2-oxazolium compounds such as 2-ethyl- 5-phenyl-1,2-oxazolium-3-sulphonate or propanephosphonic anhydride or isobutyl chloroformate or benzotriazolyloxytris-(dimethylamino)phosphonium hexafluorophosphate or diphenyl phosphoramidate or methanesulphonyl chloride or thionyl chloride, trifluoroacetic anhydride, if appropriate in the presence of bases such as triethylamine, pyridine or N-ethylmorpholine or N-methylpiperidine or dicyclohexylcarbodiimide and N-hydroxysuccinimide, alkoxycarbonylsulphonyltrialkylammonium hydroxides, acetic anhydride/ NaOAc/phosphoric acid, mineral acids, such as, for example, sulphuric acid, or organic sulphonic acids such as, for example, p-toluenesulphonic acid. Thionyl chloride/ pyridine is preferred.

The reaction of the compounds of the general formula (IV) is in general carded out in a temperature range from 0° C. to 150° C., preferably from 30° C. to 80° C.

The reaction can be carried out at normal pressure, but also at elevated or reduced pressure (e.g. 0.5 to 3 bar). In general the reaction is carried out at normal pressure.

Suitable solvents for the alkylation am also customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dimethylformamide is preferred.

Suitable bases are in general alkali metal hydrides or alkoxides, such as, for example, sodium hydride or potassium tert-butoxide, or cyclic amines, such as, for example, piperidine, dimethylaminopyridine or $C_1$–$C_4$-alkylamines, such as, for example, triethylamine. Sodium hydride is preferred.

The reaction temperatures can be varied within a relatively wide range. In general the reaction is carried out between +10° C. and +150° C., preferably between +20° C. and +100° C., in particular at room temperature.

The alkylation is carried out in the abovementioned solvents at temperatures from 0° C. to +150° C., preferably at room temperatures to +100° C.

The reactions can be carried out at normal pressure, but also at elevated or reduced pressure (e.g. 0.5 to 3 bar). In general the reactions are carried out at normal pressure.

The base is in general employed in an amount from 1 mol to 5 mol, preferably from 1 mol to 2 mol, in each case relative to 1 mol of the compounds to be alkylated.

Suitable bases for the acylation are inorganic or organic bases. These preferably include alkali metal hydroxides such as e.g. sodium hydroxide or potassium hydroxide, alkaline earth metal hydroxides such as e.g. barium hydroxide, alkali metal carbonates such as sodium carbonate or potassium carbonate, alkaline earth metal carbonates such as calcium carbonate, or organic amines, e.g. trialkyl($C_1$-$C_6$)amines such as triethylamine, or heterocycles such as pyridine, methylpiperidine, piperidine or morpholine. Triethylamine is particularly preferred.

Suitable solvents for the acylation are also customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned or even to employ the respective acylating agent as a solvent. Acetic anhydride and pyridine are preferred.

The acylation in general proceeds in a temperature range from 0° C. to +120° C., preferably at +30° C. to +90° C. and at normal pressure.

The hydrolysis of the carboxylic acid esters is carried out by customary methods, by treating the esters in inert solvents with customary bases.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (e.g. from 0.5 to 5 bar).

Enantiomerically pure forms are obtained e.g. by separating diastereomer mixtures of the compounds of the general formula (Ia or b) in which $R^1$ is an optically active ester radical, by a customary method, then either directly transesterifying or first preparing the chiral carboxylic acids and then preparing the enantiomerically pure compounds by esterification.

The separation of the diastereomers is in general carried out either by fractional crystallization, by column chromatography or by countercurrent distribution. Which is the optimum process must be decided from case to case; sometimes it is also expedient to use combinations of the individual processes. Separation by crystallization or countercurrent distribution or a combination of both processes is particularly suitable.

The enantiomerically pure compounds are also accessible by chromatography of the racemic esters on chiral phases.

The amines of the general formula (III) are known.

The compounds of the general formula (IV) are known or can be prepared, for example, as described above.

The compounds of the general formula (II) are known or can be prepared, for example, by reacting aldehydes of the general formula (V)

$$A-CHO \qquad (V)$$

in which

A has the meaning specified above, with two equivalents of the compounds of the general formula (VI)

$$H_3C-CO-CH_2-CO_2R^{1'} \qquad (VI)$$

in which $R^{1'}$ has the meaning specified above, in an organic solvent and in the presence of a base.

Suitable solvents are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoramide or dimethylformamide, or acetic acid or halogenated hydrocarbons such as methylene chloride, carbon tetrachloride or hydrocarbons such as benzene or toluene. It is also possible to use mixtures of the solvents mentioned. Ethanol and methanol are particularly preferred.

Suitable bases are in general alkaline metal hydrides or alkoxides, such as, for example, sodium hydride or potassium tert-butoxide, or cyclic amines, such as, for example, piperidine, dimethylaminopyridine or $C_1$-$C_4$-alkylamines, such as, for example, triethylamine. Piperidine is preferred.

The reactions can be carried out at normal pressure, but also at elevated or reduced pressure (e.g. 0.5 to 3 bar). In general the reactions are carried out at normal pressure.

The reaction temperatures can be varied within a relatively wide range. In general the reaction is carded out between +10° C. and +150° C., preferably between +20° C. and 100° C., in particular at the boiling temperature of the respective solvent.

The compounds of the general formulae (V) and (VI) are known per se or can be prepared by customary methods.

The compounds of the general formula (Ia or b) according to the invention show an unforeseeable, useful spectrum of pharmacological action.

They are modulators having selectivity for calcium-dependent potassium channels of high conductivity (BK(Ca) channels), in particular of the central nervous system.

On account of their pharmacological properties, they can be employed for the production of medicaments for the treatment of degenerative central nervous system disorders, on occurrence of dementias such as multiinfarct dementia (MID), primary degenerative dementia (PDD), presenile and senile dementia of the Alzheimer's disease type, HIV dementia and other forms of dementia, for the treatment of Parkinson's disease, amyotropic lateral sclerosis and also multiple sclerosis and sickle cell anemia.

The active compounds are furthermore suitable for the treatment of brain function disorders in old age, of organic brain syndrome (OBS) and of age-related memory disorders (age-associated memory impairment, AAMI).

They are suitable for the prophylaxis and control of the sequelae of cerebral circulatory disorders such as cerebral ischaemias, strokes, craniocerebral traumata and subarachnoid haemorrhages.

They are useful for the treatment of depressions and psychoses, e.g. schizophrenia. They are additionally suitable for the treatment of disorders of neuroendocrine secretion and of neurotransmitter secretion and health disorders connected therewith such as mania, alcoholism, drag abuse, dependence or abnormal eating behaviour. Other application areas are the treatment of migraine, sleep disorders and of neuropathy. They are moreover suitable as analgesics.

The active compounds are furthermore suitable for the treatment of disorders of the immune system, in particular of T-lymphocyte proliferation and for affecting the smooth musculature, in particular of uterus, urinary bladder and bronchial tract and for the treatment of diseases connected therewith such as e.g. asthma and urinary incontinence and for the treatment of high blood pressure, arrhythmia, angina and diabetes.

[86]Rubidium Efflux from C6-BU1 Glioma Cells

The experiments were carried out with slight changes according to the method described by Tas et al. (Neurosci. Lett. 94, 279–284, (1988). Rat C6-BU1 glioma cells are used for this.

From the data collected by liquid scintillation, the increase in the efflux produced by ionomycin above the basal efflux is calculated and set as 100%. The stimulations in the presence of test substances are then related to this value.

The present invention also includes pharmaceutical preparations which, in addition to inert, non-toxic, pharmaceutically suitable auxiliaries and excipients, contain one or more compounds of the general formula (I), or which consist of one or more active compounds of the formula (I), and processes for the production of these preparations.

The active compounds of the formula (I) should be present in these preparations in a concentration from 0.1 to 99.5% by weight, preferably from 0.5 to 95% by weight of the total mixture.

In addition to the active compounds of the formula (I), the pharmaceutical preparations can also contain other pharmaceutical active compounds.

The abovementioned pharmaceutical preparations can be prepared in a customary manner by known methods, for example using the auxiliary(ies) or excipient(s).

In general, it has proven advantageous to administer the active compound(s) of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, if appropriate it may be advantageous to deviate from the amounts mentioned, namely depending on the nature and the body weight of the subject treated, on individual behaviour towards the medicament, the nature and severity of the disorder, the type of preparation and administration, and the time or interval at which administration takes place.

| | Mobile phase mixtures: |
|---|---|
| a | Methylene chloride/AcOEt 10 + 1 |
| b | Methylene chloride/MeOH 10 + 1 |
| c | PE/AcOEt 7 + 3 |
| d | PE/AcOEt 1 + 1 |

STARTING COMPOUNDS

Example I

Diethyl 4-hydroxy-4-methyl-2-(3-nitrophenyl)-6-oxo-cyclohexane-1,3-dicarboxylate

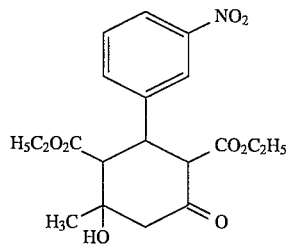

45.3 g (0.3 mol) of 3-nitrobenzaldehyde and 78 g (0.6 mol) of ethyl acetoacetate are dissolved in 300 ml of ethanol and treated with 6 ml of piperidine. The mixture is then stirred at 40° C. for 24 h. The precipitated solid is filtered off with suction and recrystallized from ethanol. 85.4 g of the title compound (72% yield) are obtained.

Example II

Diethyl 6-hydroxy-6-methyl-4-methylamino-2-(3-nitrophenyl)-cyclohex-3-ene-1,3-dicarboxylate

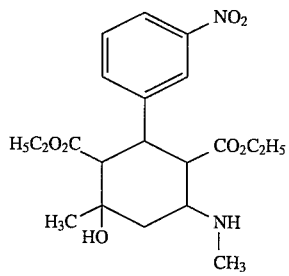

Variant A 19.7 g (50 mmol) of the compound from Example I are dissolved in 200 ml of ethanol and treated with 30 ml of a 11N methanolic methylamine solution and 1 g of TsOH hydrate. The mixture is then stirred at 60°–65° C. for 2 h. After concentrating the reaction mixture, the residue is chromatographically purified (methylene chloride) on 100 g of silica gel. The eluate is concentrated and recrystallized from diisopropyl ether. 17.0 g (84% of theory) of the title compound are obtained. M.p.: 112° C. (diisopropyl ether).

PREPARATION EXAMPLES

Example 1

Diethyl 4-methyl-6-methylamino-2-(3-nitrophenyl)cyclohexa-3,6-diene-1,3-dicarboxylate

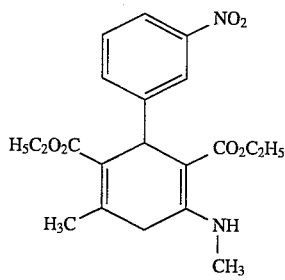

2.5 g (6.2 mmol) of the compound from Example II are initially introduced into 30 ml of pyridine, heated to 80° C. and treated with 0.95 g (80 mmol) of thionyl chloride. The mixture is kept at this temperature for 20 min and heated at reflux for a further 20 min. It is then concentrated and the residue is taken up in methylene chloride/water. The organic phase is separated off, dried over $MgSO_4$ and concentrated. Chromatographic purification on silica gel (methylene chloride:ethyl acetate 20+1) and recrystallization from isopropanol/n-heptane yield 0.8 g of the title compound (33% of theory).

The double bond isomers in each case obtained in this process are separated by chromatography and/or crystallization. The yields specified relate to isolated products.

Examples 2 and 3

Dimethyl 4-methyl-6-methylamino-2-(4-trifluoromethylphenyl)cyclohexa-3,6-diene-1,3dicarboxylate (2)

Dimethyl 6-methyl-4-methylamino-2-(4-trifluoromethylphenyl)cyclohexa-3,5-diene-1,3-dicarboxylate (3)

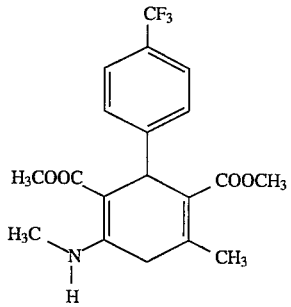

(2)

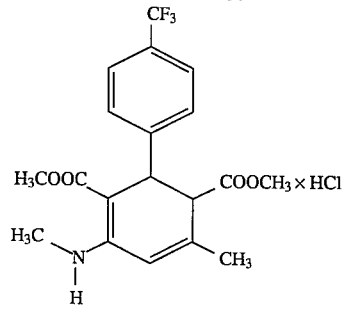

(3)

10.0 g (25 mmol) of dimethyl 6-hydroxy-6-methyl-4-methylamino-2-(4-trifluoromethylphenyl)-cyclohex-3-ene-1,3-dicarboxylate (preparation analogous to Example II) are heated to 60° C. in 100 ml of pyridine and treated with 2.5 ml of thionyl chloride. The mixture is stirred at 60° C. for 10 minutes and concentrated, and the residue is taken up in methylene chloride, washed three times with water, dried and concentrated. The residue is grossly purified on 200 g of silica gel (petroleum ether/AcOEt=3:1) and then separated by MPLC (methylene chloride/AcOEt=30:1). Two fractions are obtained. 224 mg (2.3%) of dimethyl 4-methyl-6-methylamino-2-(4-trifluoromethylphenyl)-cyclohexa-3,6-diene-1,3-dicarboxylate (non-polar isomer (2)) crystallize from ether/petroleum ether. From the 2nd fraction, 2.29 g (22%) of the polar isomer, dimethyl 6-methyl-4-methylamino-2-(4-trifluoromethylphenyl)-cyclohexa-3,5-diene-1,3-dicarboxylate (3) are precipitated from AcOEt as the hydrochloride ($R_f$=0.47 (c)).

The compounds mentioned in Tables 1 and 2 are prepared in analogy to the preparation procedures mentioned above.

TABLE 1

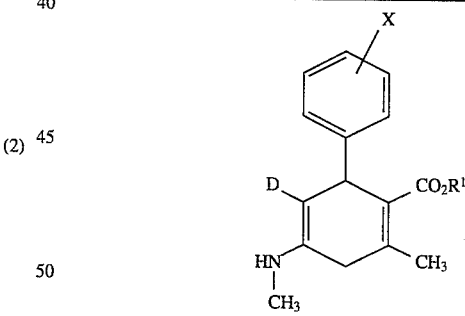

| Ex. No. | D | $R^1$ | $R_f$* | Yield (% of theory) | X |
|---|---|---|---|---|---|
| 4 | —$CO_2CH_3$ | $CH_3$ | 0.36 (c) | 7% | 3-$NO_2$ |
| 5 | —$CO_2CH_3$ | $CH_3$ | 0.34 (c) | 10% | 4-$NO_2$ |

TABLE 2

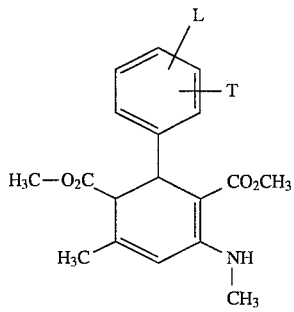

| Ex. No. | L | T | $R_f$* | Yield (% of theory) |
|---|---|---|---|---|
| 6 | 3-NO$_2$ | H | 0.33 (c) | 17 |
| 7 | 4-Cl | H | 0.44 (c) | 9 |
| 8 | 2-Cl | 3-Cl | 0.40 (c) | 25 |
| 9 | 4-NO$_2$ | H | 0.31 (c) | 15 |

We claim:

1. Cyclohexadiene derivatives of the general formula (Ia or b)

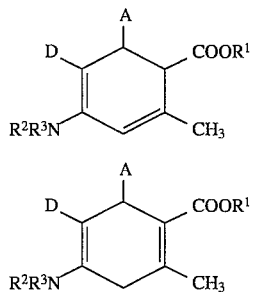

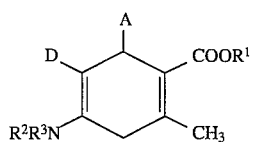

in which

A represents aryl having 6 to 10 carbon atoms or pyridyl, each of which is optionally substituted up to 3 times by identical or different substituents from the group consisting of nitro, cyano, halogen, cycloalkyl having 3 to 7 carbon atoms and trifluoromethyl or straight-chain or branched alkylthio, alkyl or alkoxy in each case having up to 6 carbon atoms, $R^1$ represents hydrogen or straight-chain or branched alkyl having up to 8 carbon atoms, $R^2$ and $R^3$ are identical or different and represent hydrogen or straight-chain or branched alkyl or acyl in each case having up to 6 carbon atoms, D represents nitro or straight-chain or branched alkoxycarbonyl having up to 8 carbon atoms, and their salts.

2. Cyclohexadiene derivatives according to claim 1, in which

A represents phenyl, naphthyl or pyridyl, each of which is optionally substituted up to 3 times by identical or different substituents from the group consisting of nitro, cyano, fluorine, chlorine, cyclopropyl, cyclopentyl, cyclohexyl cycloheptyl, bromine, iodine and trifluoromethyl or straight-chain or branched alkylthio, alkyl or alkoxy in each case having up to 4 carbon atoms, $R^1$ represents hydrogen or straight-chain or branched alkyl having up to 6 carbon atoms, $R^2$ and $R^3$ are identical or different and represent hydrogen or straight-chain or branched alkyl or acyl in each case having up to 4 carbon atoms, D represents straight-chain or branched alkoxycarbonyl having up to 6 carbon atoms, and their salts.

3. Cyclohexadiene derivatives according to claim 1 in which

A represents phenyl or pyridyl, each of which is optionally substituted up to 3 times by identical or different substituents from the group consisting of nitro, cyano, fluorine, chlorine, bromine, cyclohexyl, iodine, trifluoromethyl, methyl and methoxy or methylthio, $R^1$ represents hydrogen or straight-chain or branched alkyl having up to 4 carbon atoms, $R^2$ and $R^3$ are identical or different and represent hydrogen or straight-chain or branched alkyl or acyl in each case having up to 3 carbon atoms, D represents straight-chain or branched alkoxycarbonyl having up to 4 carbon atoms, and their salts.

4. Cyclohexadiene derivatives according to claim 1 wherein such compound is Dimethyl-4-methyl-6-methylamino-2-(3-nitrophenyl)-cyclohexa-3,6-diene-1,3-dicarboxylate of the formula

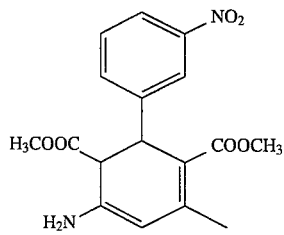

and salts thereof.

5. Cyclohexadiene derivatives according to claim 1 wherein such compound is Dimethyl-6-methyl-4-methylamino-2-(3-nitrophenyl)-cyclohexa-3,5-diene-1,3-dicarboxylate of the formula

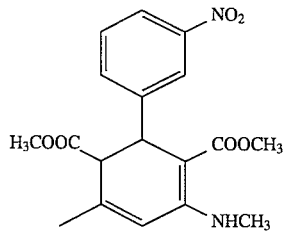

and salts thereof.

6. A composition for the treatment of degenerative central nervous system disorders comprising an amount effective therefor of a compound or salt thereof according to claim 1 and a pharmacologically acceptable diluent.

* * * * *